(12) United States Patent
Roger et al.

(10) Patent No.: US 6,544,266 B1
(45) Date of Patent: Apr. 8, 2003

(54) METHOD AND APPARATUS FOR DELIVERING BIO-ACTIVE COMPOUNDS TO SPECIFIED SITES IN THE BODY

(75) Inventors: Gregory James Roger, Crows Nest (AU); Mervin John Cross, Crows Nest (AU)

(73) Assignee: Australian Surgical Design and Manufacture PTY, Ltd., Miranda (AU)

( * ) Notice: Subject to any disclaimer, the term of this patent is extended or adjusted under 35 U.S.C. 154(b) by 0 days.

(21) Appl. No.: 09/889,797

(22) PCT Filed: Jan. 14, 2000

(86) PCT No.: PCT/AU00/00020

§ 371 (c)(1),
(2), (4) Date: Jan. 4, 2002

(87) PCT Pub. No.: WO00/42929

PCT Pub. Date: Jul. 27, 2000

(30) Foreign Application Priority Data

Jan. 22, 1999 (AU) .............................................. PP8304

(51) Int. Cl.⁷ .............................................. A61B 17/56
(52) U.S. Cl. .............................. 606/70; 606/87; 606/86; 606/69
(58) Field of Search ............................... 606/87, 70, 61, 606/69, 86, 72, 71

(56) References Cited

U.S. PATENT DOCUMENTS

| 4,772,261 A | | 9/1988 | Von Hoff et al. | |
| 5,053,039 A | * | 10/1991 | Hofmann et al. | 606/86 |
| 5,324,290 A | * | 6/1994 | Zdeblick et al. | 606/61 |
| 5,492,697 A | | 2/1996 | Boyan et al. | |
| 5,569,251 A | | 10/1996 | Baker et al. | |
| 5,620,448 A | * | 4/1997 | Puddu | 606/83 |
| 5,634,926 A | | 6/1997 | Jobe | |
| 5,713,899 A | | 2/1998 | Marnay et al. | |
| 5,749,875 A | * | 5/1998 | Puddu | 606/69 |
| 5,766,251 A | | 6/1998 | Koshino | |
| 5,938,664 A | * | 8/1999 | Winquist et al. | 606/62 |
| 6,068,593 A | * | 5/2000 | Krauter et al. | 600/135 |

FOREIGN PATENT DOCUMENTS

| EP | 0773004 | 5/1997 |
| FR | 2764183 | 12/1998 |
| WO | WO 8806023 | 8/1988 |
| WO | WO9201428 | 2/1992 |
| WO | WO9737620 | 10/1997 |
| WO | WO9952473 | 10/1999 |

* cited by examiner

Primary Examiner—Pedro Philogene
(74) Attorney, Agent, or Firm—Hunton & Williams (57) ABSTRACT

The present invention discloses an apparatus for delivering bio-active substances to specified sites of action in the course of performing surgical procedures and particularly of performing surgical procedures requiring reconstructive orthopaedic intervention. It further relates to referred constructions of such apparatus so that it is best adapted for use in the performance of surgical procedures requiring reconstructive orthopaedic intervention, especially high tibial osteotomies and mandibular, or other skull bone, reconstructions. Additionally disclosed is a method for implanting an apparatus according to the invention, as well as a method for performing tibial osteotomies using the apparatus of the invention.

26 Claims, 8 Drawing Sheets

METHOD AND APPARATUS FOR DELIVERING BIO-ACTIVE COMPOUNDS TO SPECIFIED SITES IN THE BODY

FIELD OF THE INVENTION

The present invention relates to a method and apparatus for delivering bio-active compounds to specified sites of action in the course of performing surgical procedures and particularly of performing surgical procedures requiring reconstructive orthopaedic intervention. It further relates to preferred constructions of such apparatus so that it is best adapted for use in the performance of surgical procedures requiring reconstructive orthopaedic intervention, especially high tibial osteotomies and mandibular, or other skull bone, reconstructions.

BACKGROUND ART

It is known that the delivery of bio-active substances, such as bone morphogenic protein, to surfaces of bone can encourage bone growth. It is also known that when other bio-active substances are delivered to injured body tissues, for example, those tissues injured in the course of performing invasive surgical procedures, they may catalyse the healing process or carry out other desirable actions including preventing bleeding or excessive healing.

There is a variation in devices which can be implanted into the body of a patient during surgical procedures requiring reconstructive orthopaedic intervention. In cases where it is preferred to deliver bio-active substances to a desired site of action, for example, to the cut surfaces of bone comprising a wedge osteotomy or to a cut surface of bone exposed during mandibular or other skull bone reconstruction, such bio-active substances can be delivered to those sites of action via means of conventional delivery devices. However, when using conventional deliver devices, the bio-active substances must be delivered during the operation and before closure of the incision.

In the case of skull bone reconstructions, it is known to use wire gutters as scaffolding along which, it is aimed, bone will grow. While the application of bio-active substances to surfaces of bone may encourage bone growth, a device which provided a means to ensure that bone was encouraged to row in a particular direction at a particular location would offer a considerable improvement to existing methods for achieving that result.

In the case of high tibial osteotomies, there are a number of additional issues which the present invention addresses and which require further comment.

High tibial osteotomy is an operation that is commonly used to straighten "bowed legs" or less commonly to correct "knock knees". If a patient has either of these conditions the weight transmission through the knee is passed more to one side of the centre of the tibia than the other, resulting in excessive wear on that side of the patients knee. In the case of "bowed legs" the weight will be borne predominantly on the medial side of the knee and thus excessive wear will occur on that side of the patients knee. Often the wear will occur first, leading to bowing of the leg and then the wear accelerates. A positive feedback situation is thus created and the problem will be exacerbated with time unless there is surgical intervention.

Conventionally patients with this condition are given a number of choices of surgical intervention. In older patients it is usual to carry out a total knee replacement as the knee is often in a deteriorated state. In younger patients the choice is often to carry out a high tibial osteotomy. The best known procedure for this operation is to approach the upper end of the tibia from the lateral side and to fix the tibia in a more favourable alignment. This can be done either by removing a wedge of bone (referred to as a closing wedge) or by making a dome shaped cut, rotating the tibia and refixing the tibial plateau relative to the tibial shaft. In either of the above cases fixation of the "fracture" created by the saw cut during the osteotomy is required. This may be achieved using a plaster cast, staples, staple plates or plates and screws.

It is also known to approach the operation from the more worn side of the tibia and to provide an opening wedge. In this case a cut is made across the tibia and the worn side is elevated to give the tibial plateau a more favourable alignment.

There are a number of problems associated with the traditional approaches to carrying out high tibial osteotomy. The aim of the operation is to realign the tibia so that, in the case of "bowed legs", the foot is swung outwardly and the weight is carried with an over correction of, typically, about 3° so that the lateral side of the joint gets more weight and the medial side can recover. This arrangement has been found preferable as compared with giving equal weighting to both sides of the joint.

Intra-operatively it is difficult to apply the correct angle of adjustment. In the closing wedge situation the correct thickness of wedge must be taken from the patient. If the second cut is not at the right angle it has been found very difficult to make a third cut to correct the angle. In the case of the domed osteotomy the actual angle of shift of the tibia is difficult to determine accurately. In either it is difficult to reliably set within 2° of the desired angle. It has been found a little easier to determine the right angle in the case of an opening wedge however this has substantial difficulties as will be explained in the following paragraph.

Fixation of the fracture created surgically is a problem in respect of all of the known methods of high tibial osteotomy however it is a particular problem in connection with the opening wedge operation. There is great force to close the wedge from gravity and from muscle forces. There is also the problem that bone requires some compression to heal so that a bone held open tends not to fill with bones The latter problem has been tackled by packing the open wedge with bone harvested from elsewhere on the patient The former problem has been approached by the use of a plate and screws to hold the gap open. These approaches have failed due to collapse of the bone graft before it has time to strengthen and heal, and failure of the plate to hold the bones apart. This latter failure occurs because there is only room for one screw above the osteotomy so that there is no rotational control of the plate which tends to collapse by twisting or shearing out of the bone. Even if two screws could be placed the forces are so great that screws can be ripped out of the bone.

In the case of surgical intervention on the lateral side of the knee there is a problem that the cut is near a major nerve and the incision is incompatible with subsequent incisions should a total knee replacement be required. Too many incisions in a limited area causes compromise of the blood supply to the skin and to underlying tissues creating a risk of these tissues failing to heal after surgery. Operations from the lateral side also have the problem that the fibula, which lies adjacent the lateral side of the tibia must also be cut and shortened.

Secondary alignment issues are also hard to control with the known methods of high tibial osteotomy. The osteotomy should be done exactly in the medial-lateral plane. There should be no posterior tilt, nor rotation about the axis of the tibia. If such misalignments are introduced by the operation other deformities are introduced into the long axis of the tibia. These problems are particularly severe in the case of the closing wedge operation as in that case two incisions have to be made in the bone rather than one in an opening wedge procedure. In addition the two cuts of the closing wedge osteotomy must meet exactly at the cortex of the bone on the side thereof opposite to the side on which the wedge is to be removed. As such, the cortex of the bone on that side will remain intact thereby acting as a stabilising means for the whole procedure. The absence of such stabilising means would considerably increase the risk of the procedure failing.

In order to overcome many of these problems Puddu (U.S. Pat. No. 5,749,875) designed a system for performing proximal tibial (or femoral) osteotomies which includes a plurality of bone plates of various sizes, and a calibrated wedge tool for opening a resected tibial wedge and determining the size plate to use in the osteotomy. However, a known complication of securing plates to bones across areas which will be subjected to weight bearing forces, such as across a widened edge of a high tibial wedge osteotomy, is that ultimately shearing forces applied to the heads of screws or other instruments used to secure the plate to the bone, may cause the head of such securing means to be broken off. Such an occurrence can lead to drastic consequences which may require the patient to undergo further surgery. It is necessary, therefore, to incorporate a means within such plates so that shearing forces applied to the heads of the securing devices which secure the plate across the widened edge of a wedge osteotomy are minimised to the greatest degree possible.

The present invention is directed to providing an alternative and improvement to the existing techniques and apparatus for use in the performance of surgical procedures, especially those requiring reconstructive orthopaedic intervention, such as high tibial osteotomies and mandibular or other skull bone reconstructions.

DESCRIPTION OF THE INVENTION

In a first aspect the present invention consists in a device for use in surgery, the device comprising:

a a plate member having a longitudinal axis, a first end, a first orifice adjacent the first end, a second end, and a second orifice adjacent the second end, wherein the first orifice is circular in shape and the second orifice is ovoid or elongate in shape, the second orifice having a long diameter and a short diameter and being oriented such that the long diameter is longitudinally aligned with the longitudinal axis of the plate member, and at least one spacer member which is engageable or integral with the plate member intermediate the first and second ends of the plate member, the spacer member having a built-in substance delivery system, the substance delivery system being such that when the device has been placed in a desired location in the body of a patient at least one selected substance can be delivered from the at least one spacer member into at least one designated site of action.

In a second aspect the present invention consists in a device for delivering substances to a designated site of action in the body of a patient, the device comprising:

a plate member that is securable to a bone, the plate member having at least one spacer member that is engageable or integral with a face of the plate member, and a substance delivery system housed by the at least one spacer member in such a way that the substance delivery system can deliver at least one substance to a designated site of action in the body of a patient.

Preferred embodiments disclose that securing means are used to secure the plate member to a bone. Preferable securing means include screws and pins. However, any securing means capable of securing the plate member to a bone can be used. Furthermore, various forms of adhesives or cements can be used as an alternative or in addition to the securing means to ensure that the device is satisfactorily secured.

In a third aspect, the present invention consists in a method for implanting a device according to the first aspect of the invention during various surgical procedures, including the steps of:

a) preparing any bio-active substance or combination of such substances to be delivered to a desired site of action, and loading such preparation into the substance delivery system in the spacer member;

b) determining an appropriate location for the device so that the spacer member containing the bio-active substance delivery system is aimed in the direction of the desired site of action for the bio-active substance; and c) securing the device to a bone in the body of a patient.

The device according to this invention may be used in the process of performing a range of surgical procedures involving reconstructive orthopaedic intervention. However, manipulation of the invention for use in this application is not to be understood as limited to such surgical procedures only. The device may also be used in other surgical procedures where it would be desirable to give effect to a spacer member and/or to deliver at least one bio-active substance to a particular site of action.

In preferred embodiments of the invention wherein a device will be placed at a location at which the head of a securing means used to secure the device to a bone in the body of a patient may be subjected to weight bearing forces, such as to a long bone in the leg of a patient wherein the device is secured so that its long axis remains parallel to a weight bearing axis of the bone, the function of the ovoid or elongate shaped orifice at the second end of the plate member becomes increasingly valuable: provided that the plate member is secured so that its long axis remains parallel to the weight bearing axis of the bone, the long diameter of the ovoid or elongate shaped orifice will, according to this invention, also be largely parallel to, and in the same plane as the weight bearing axis of the bone. Once so secured, such embodiments of the invention will provide the plate member with an ability to make slight movements in the same plane as the weight bearing axis of the bone to which it is secured, such movement being limited only by the length of the long diameter of the ovoid or elongate shaped orifice. This will considerably reduce any shearing forces upon the head of the securing means which has been passed through the ovoid or elongate orifice, when, post-operatively, the patient bears weight on the bone to which the device has been secured; as, for example, during the stance phase of a gait cycle.

In particular embodiments of the invention wherein a device will be placed at a location at which the head of a securing means used to secure the device to a bone in the body of a patient may be subjected to weight bearing forces, such as across a widened end of a high tibial wedge osteotomy, it will be necessary to ensure that the plate member is positioned such that the second end of the plate member is secured to the bone on the distal side of the wedge osteotomy. This is because tibial wedge osteotories are typically cut at a location on the tibia which is extremely proximal to the knee joint. By placing the device such that the second end of the plate member, adjacent to which is the ovoid or elongate shaped orifice, is secured to the bone on the distal side of the wedge osteotomy, it is possible to ensure that any movement of the plate member in the plane of the weight bearing axis of the bone to which it is secured, will not cause an end of the plate member to encroach into the immediate vicinity of the knee joint: the end of the plate member nearest the knee joint being the first end, adjacent to which is the circular orifice; the shape of which prevents any movement of the plate member once a securing means has been passed through it and into the bone.

In alternative embodiments of the invention wherein it is desirable to deliver at least one bio-active substance to a designated site of action, such as to a cut surface of bone, it will be necessary to ensure that the plate member is positioned such that a spacer member containing a substance delivery system points in the desired direction and the substance delivery system can perform its function by delivering a bicactive substance or substances to the designated site of action.

As disclosed by the first and second aspects of the invention, in some preferred embodiments, the plate member and spacer member of the device are two distinct components of the invention which are engageable with one another. Such embodiments provide the opportunity for plate members and spacer members of different shapes and sizes to be engaged for implantation. Accordingly, the surgeon is placed in a position to determine the most appropriate shape and size for each component of the invention in order to suit the circumstances of each case. For example, the most appropriate size and shape for the spacer member may be dependent on the dimensions of a wedge into which the spacer member is finally located following implantation of the device. Similarly, the most appropriate size and shape for a plate member may be dependent on anatomical considerations, such as the available surface area of bone to which the plate member is finally secured, the size of the gap defined by, for example, the widened cut of a wedge osteotomny, as well as the relative density of the bone to which the device is secured.

A further advantage arising from embodiments in which the plate member and spacer member are distinct but engageable components of the device is that one can be removed before the other. Having particular regard to prior art devices, the plate member is the most superficial part of a device once the device is implanted. This often results in a subcutaneous lump and may sometimes be painful for the patient. Because the device according to some preferred embodiments of the present invention is such that the plate member is simply engageable (and not necessarily integral) with the spacer member, this ensures that the plate member can be removed from the patient prior to removal of the spacer member. In other words, even if, for example, the gap created by a wedge osteotomy is not yet completely filled and still requires the presence of the spacer member, provided that healing is sufficient, the plate member can be removed. The result being that the subcutaneous lump is removed, as well as any potential pain associated with the presence of the plate member.

In a fourth aspect the present invention relates to a process for carrying out a high tibial osteotomy which incorporates a device described in the first aspect of the invention, the process including the steps of:

a) forming a saw cut in a tibia of a patient substantially in the medio-lateral plane adjacent to the head of the fibula;

b) causing the cut to be widened on one side so as to bring the axis of the tibia into a desired alignment;

c) placing the device such that the plate member spans the gap defined by the widened cut, the second end of the plate member is positioned on the distal side of the wedge osteotomy, and at least one spacer member protrudes into the gap defined by the widened cut such that cortical bone on either side of the gap is in contact with the spacer member; and d) securing the device to the tibia.

It will be appreciated that in order to be sure that for any given patient the correct angle is maintained between the parts of the tibia the surgeon will need to have a number of the devices available each with at least one spacer member the width of which will vary from one device to another. After the tibia has been transected and the cut widened the surgeon can measure the width of the gap between the cut edges of bone and select a device with an appropriately sized spacer member. In this case the ends of the spacer member on a face of the plate will contact the cortical bone on either side of the cut with the axis of the tibia in its desired alignment. In an alternative embodiment of the present invention the plate may be provided with a spacer member, or more than one, that is of adjustable width. Using this embodiment of the invention, the surgeon can have available a single plate and adjust the width of the spacer member (or spacer members) thereon in accordance with the needs of the particular patient being operated upon. As a part of the technique of performing such embodiments of the invention, it may also be desirable to implant various resorbable bases, such as resorbable bone fillers, along with the plate, as they have considerable structural benefit.

In a preferred embodiment of the invention the operation is commenced on the side of the tibia that is most worn. In the case of an operation to treat bowed legs, for example, this means that the initial incision will be on the medial side of the tibia. This has the advantage that the operation will not make more difficult a subsequent total knee replacement operation, should that be necessary.

It is preferred, when making a cut into the tibia that the cut stops short of cutting right through that bone. An uncut section of cortical bone on the side opposite to the incision, will provide a stabilising means for the whole procedure and, at the same time, have enough resilience to bend slightly allowing the desired correction of the axis of the tibia to be made. The cut is guided in preferred embodiments of this invention in the medio-lateral plane by a pair of rods placed into holes drilled in the tibia which are aligned with one another in that plane. During placement of the rods it is possible for the surgeon to accurately measure the width of the tibia in the plane of the cut and to then ensure that the cut does not extend right through the tibia.

A spreading tool is preferably inserted into the cut in order to spread it to the desired extent This tool is preferably able to hold the tibia in the correct alignment while the plate is affixed to the tibia. With the gap on the one side of the tibia held open by the spreading tool it is possible to position the plate, with the spacer member extending into the gap and contacting the cortical bone on each side of it, and position securing means, through the plate and into the bone on either side of the cut.

It is preferable that after the plate is secured to the tibia on either side of the cut that the gap between the two faces of the tibia are packed with bone. It is particularly preferred that bi-cortical bone harvested from the patient's iliac crest be used for this purpose. Alternatively a bone growth stimulating filler material, such as bone morphogenic protein, could be used to pack between the two bone surfaces, with or without resorbable artificial bone. Subject to obtaining an appropriate preparation of such bone growth stimulating filler material, such as a liquid preparation, it is possible to deliver the material to a desired site of action via the substance delivery system.

In general, it is because the performance of surgical procedures causes injury to the surrounding tissue, that it may be desirable to deliver various bio-active substances to certain sites within the injured tissues in order to catalyse the healing process, or for some other purpose, such as to encourage bone growth on the cut surface of bone following osteotomy. In fact, given that the device is placed at or within the site of injury, the device itself is in an excellent position to apply any chemicals or hormones which may promote such healing, or carry out any other such desired actions including preventing bleeding or excessive healing.

In preferred embodiments of the invention wherein the device is being used for reconstructive purposes, such as in rebuilding the mandible bone in a patient, the substance delivery system may be of particular value. In such embodiments of the invention the plate member may act as a scaffold only and, accordingly, the substance delivery system can be used to ensure that a bio-active substance or substances which promote bone growth are delivered to the area, therefore encouraging bone to grow along the plate member.

There is at least one preferred mechanism whereby the flow of the bio-active substance from the substance delivery system can be controlled. This is by means of restricted orifices through which the bio-active substance leaks ("leak delivery system").

In a preferred embodiment of the invention wherein the "leak delivery system" is the chosen means for controlling the delivery of bio-active substance from the substance delivery system, such delivery system will comprise of at least one chamber created within the body of a spacer member of the device; and at least two restricted orifices cut into the surface of the spacer member providing a passage through a first orifice, through the chamber of the substance delivery system, and out through another second orifice. Bio-active substances may be loaded into the chamber of the substance delivery system via means of conventional delivery apparatus, such as a syringe loading system. With the exception of the at least two orifices, the cavity is sealed and the continuous force of the substance or bodily fluid being delivered through a first orifice causes the substance to leak out through another second orifice onto the site of action.

In an alternative embodiment of the invention wherein such a "leak delivery system" is the chosen means for controlling the delivery of a bio-active substance from the substance delivery system, the use of blood pressure as a means of causing the bio-active substance to flow from the delivery system onto the site of action is a preferred mechanism. In such circumstances, it is necessary that the substance delivery system is pre-loaded with the desired substance or substances and that the device be placed so that a first orifice on the surface of the spacer member rests against a source of bleeding tissue, such as the cut surface of a bone following orthopaedic intervention. In this case, as blood exudes from the injured bone surface it leaks into the first orifice and consequently causes any bio-active substance already present in the cavity of the delivery system to leak out the second orifice onto the site of action.

In a further embodiment of the invention representing a refinement of the apparatus comprising the device to be used in the performance of the invention wherein a "leak delivery system" is the chosen means for controlling the delivery of a bio-active substance from the substance delivery system, a hollow tubular structure may extend from the second orifice of the substance delivery system. The tubular structure should be made of an impermeable material, and have within a wall of the structure at least one orifice.

Characteristic of this embodiment of the invention is the presence of a passage leading in through the first orifice of the substance delivery system; through the cavity contained in a spacer member of the invention; through the second orifice of the substance delivery system; through the tubular structure; and out through the at least one further orifice in a wall of the tubular structure. As described in some of the foregoing embodiments of the invention, with the exception of the at least one first orifice in the substance delivery system and the at least one further orifice in a wall of the tubular structure extending from a second orifice in the substance delivery system, there are no other means for a bio-active substance which is present at any position of the passage defined by the components of the present embodiment, to escape.

The invention according to this embodiment is particularly useful in the performance of surgical procedures requiring reconstructive orthopaedic intervention, such as, the reconstruction of a mandible bone in the body of a patient. Such a procedure typically involves the use of a wire mesh in the shape of a gutter, with a trough running along its length, as a replacement means for resected or absent segments of the mandible bone. The wire gutter is intended to act as a scaffolding and support along which bone may grow. In the case of performing this surgical procedure on a patient, the embodiment of the invention in which a tubular structure extends from a second orifice in the substance delivery system is manipulated such that the tubular structure is positioned in the trough of the wire gutter along its length. At least one orifice within a wall of the tubular structure is pointed such that it aims in the direction of the desired site of action for the bio-active substance.

In an embodiment of the invention wherein there is a plurality of orifices within a wall of the tubular structure, it becomes possible to deliver at least one bio-active substance to a large surface area of bone, thereby, for example, encouraging the bone to grow all along the length of the wire gutter scaffolding. As described in foregoing embodiments of the invention, it may be possible to use blood pressure leaking from a cut surface of bone for the purpose of causing at least one bio-active substance to be pushed through the passage created by the components of this embodiment of the invention and out of a plurality of orifices in a wall of the tubular structure to a desired site of action. Alternatively, it may be necessary to use other means, such as, a suction device, to draw adequate bio-active substance through the passage.

The foregoing embodiments which describe various mechanisms that can be used in controlling the flow of bio-active substance from a substance delivery system are by no means intended to represent an exhaustive list as there are a number of other possible arrangements which may achieve the same result.

BRIEF DESCRIPTION OF THE DRAWINGS

By way of example, preferred embodiments of the invention are described with reference to the accompanying drawings in which.

BEST MODE CARRYING OUT INVENTION

In different embodiments, the device 10 may be used in the course of performing various surgical procedures including those requiring reconstructive orthopaedic intervention such as high tibial osteotomies and mandibular or other skull bone reconstructions.

When the device 10 is to be used in the process of performing a high tibial osteotomy, the device is adapted for implantation into a patient in order to be secured to the tibia 11 across the widened end of a wedge osteotomy 12.

Figure 1:
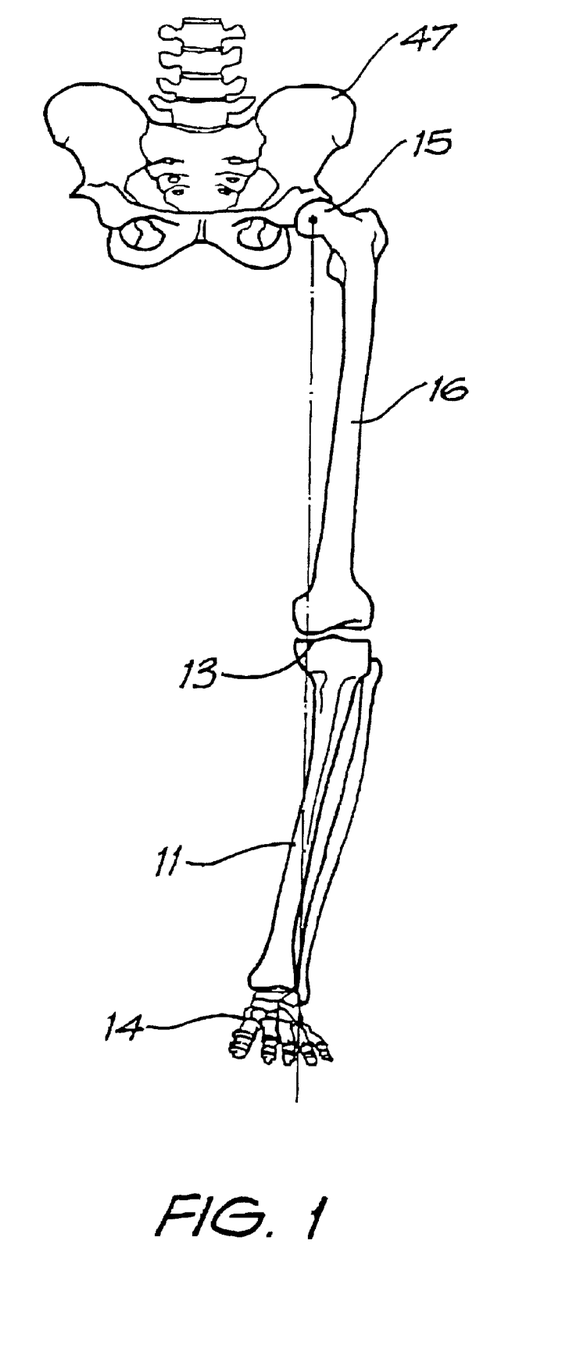
FIG. 1 is an anterior view of the leg bones of a patient showing the knee joint wear typical of bowed legs.
Figure 2:
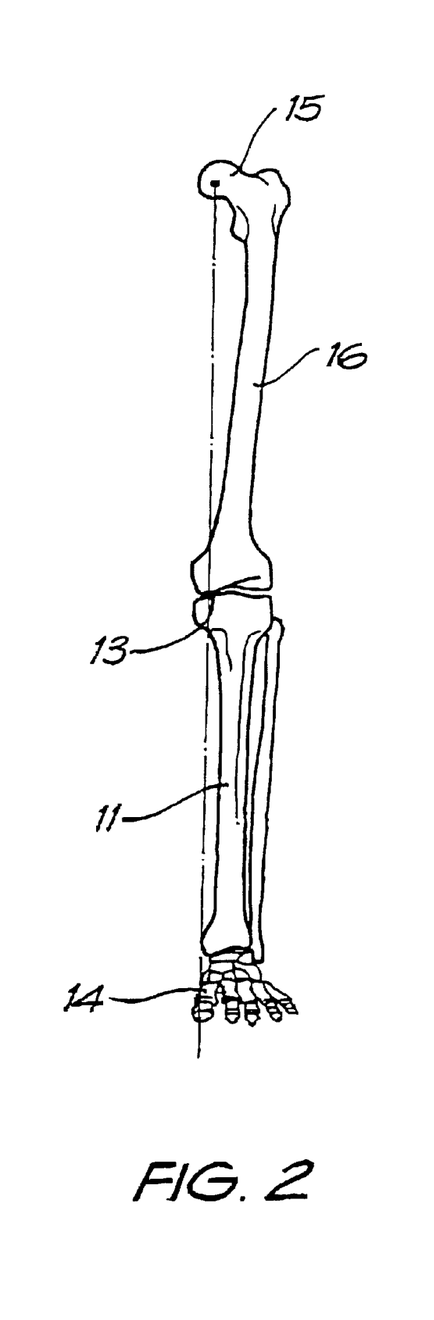
FIG. 2 is an anterior view of the leg bones of such a patient after a high tibial osteotomy.

As is seen in FIG. 1 a patient with a bowed leg will exhibit a tibia 11 with a plateau having a worn medial side 13. This allows the tibia 11 to angle inwardly so that the foot 14 is considerably further towards the mid-line of the body than it should be. FIG. 2 shows the effect of a high tibial osteotomy on such a patient. The foot 12 has been moved laterally such that it now lies outside of a vertical line from the head 15 of the femur 16 to the ground. This is a slight over correction to ensure that the weight of the patient falls slightly more heavily on the more lightly worn lateral surface of the plateau of the tibia 11.

Figure 3:
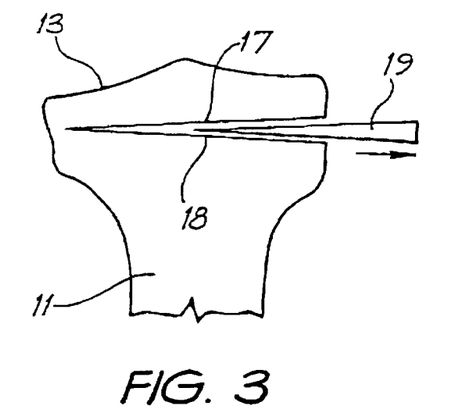
FIG. 3 is an anterior view of a high tibial osteotomy by the prior art closing wedge technique.
Figure 4:
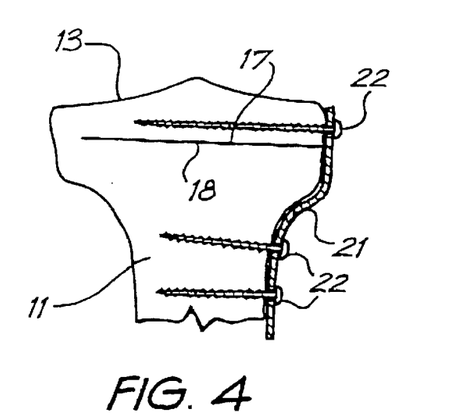
FIG. 4 is an anterior view of the tibia of FIG. 3 after completion of the osteotomy.

The most common way in which such a deformity is treated is illustrated in FIGS. 3 and 4. An incision is made on the lateral side of the tibia 11 and two cuts 17 and 18 are made in the tibia 11 just below its head to allow a wedge of bone 19 to be removed from the lateral side of the tibia 10. The foot 12 and the lower end of the tibia 10 can then be moved laterally and, as is seen in FIG. 4, the surgically induced fracture fixed by the use of a plate member 21. The plate member 21 is held in place on the tibia by securing means 22 extending through the plate member 21 and into the tibia 10 both above and below the saw cuts 17 and 18.

As has been indicated above this known procedure has a number of problems. The present invention will now be described with reference to FIGS. 5 to 14.

Figure 5:
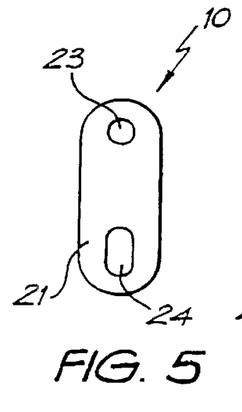
FIG. 5 is a posterior view of a device for use in the method according to the present invention.
Figure 6:
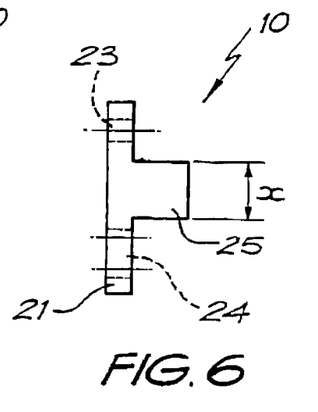
FIG. 6 is a lateral view of the device of FIG. 5.
Figure 7:
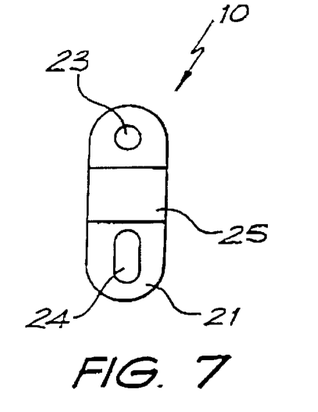
FIG. 7 is a anterior view of the device of FIG. 5.

The surgeon conducting the high tibial osteotomy will have a number of devices 10 as shown in FIGS. 5 to 7. Each device 10 comprises a planar backing plate 21 which has an orifice at each end; one orifice 23 is circular in shape and the other orifice 24 is ovoid or elongate in shape. On a face of the plate member 21 a spacer member 25 extends laterally. The spacer member 25 has a width 'x'. Individual devices 10 may have different widths 'x' so that the surgeon may select an appropriate one of them for use in any particular operation.

Figure 8:
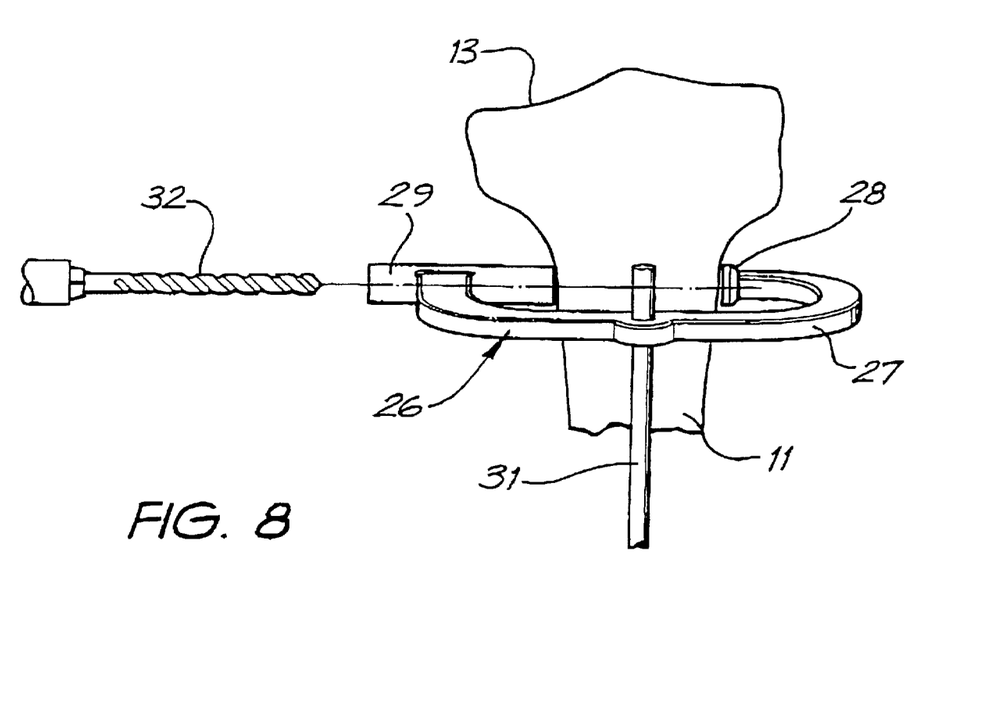
FIG. 8 is an anterior view of a step in the method according to one preferred embodiment of the present invention in which a first guide hole is being drilled in a tibia.

The operation commences with the surgeon making a small medial incision (not shown) in the patient and placing a c-arm drill guide 26 on the tibia 11. The c-arm clamp 25 has a c-shaped body 27 that at one end 28 is adapted to bear against the skin of the patient and at the other end has a drill guide tube 29 that can be moved in and out relative to the body 27 to clamp it in place on the patient. An elongate guide arm 31 extends from the body 27 of the c-arm drill guide. In use the c-arm drill guide 26 is positioned so that the drill guide tube is about 25 mm distal to the joint line of the knee and on the medial side of the tibia 11. The guide arm 31 is then aligned with the axis of the tibia 11 to ensure that the guide tube 28 is aligned at right angles to that axis.

Figure 9:
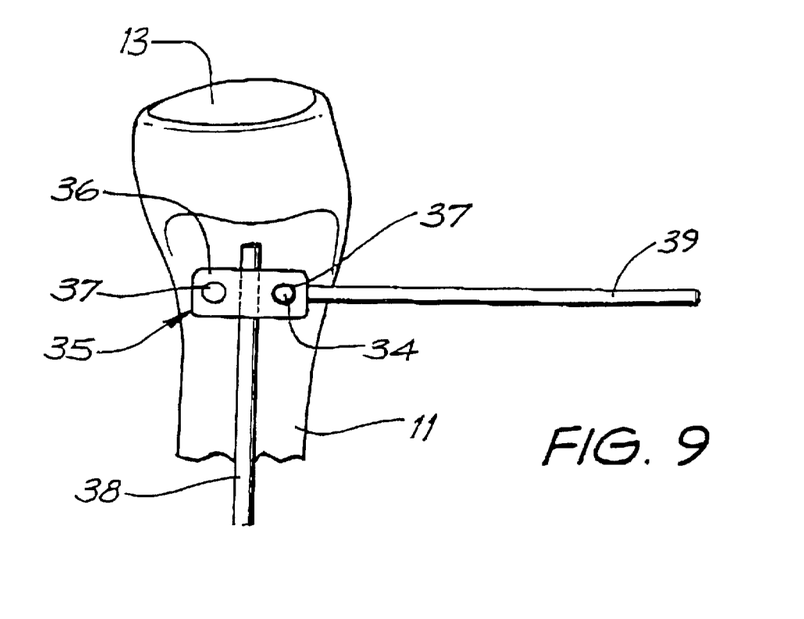
FIG. 9 is a medial view of a guide member used to assist in the placement of a second guide hole in the tibia shown in FIG. 8.
Figure 10:
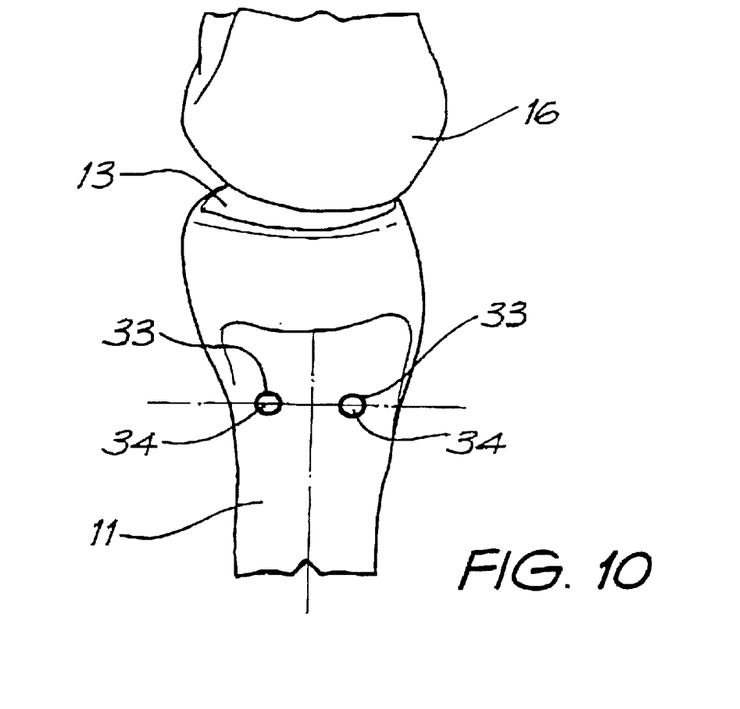
FIG. 10 is medial view of the tibia of FIG. 8 after a pair of guide pins have been placed into the guide holes drilled therein.

A drill bit 32 is then introduced into the drill guide tube 29 and caused to rotate to drill a 3.2 mm diameter hole 33 through the full thickness of the tibia in the medio-lateral plane in which a cut will subsequently be made. The width of the tibia 11 at this point is then accurately measured through this hole. A blunt pin 34 is then placed in the hole with a length sufficient that the pin protrudes about 30 mm from the medial side of the tibia 11. A parallel drill guide 35 is placed on the pin 34. The guide 35 comprises a plate 36 that has two spaced apart holes 37 in it and an elongate arm 38 extending from the plate 35 at right angles to the alignment of the holes 37. A handle 39 extends laterally from the plate 35. One of the holes 37 is slid over the blunt pin 34. The arm 38 is aligned with the axis of the tibia and another 3.2 mm hole 33 is drilled into the tibia 11 through the second of the holes 37 in the plate 35. This procedure results in a pair of holes 33 being formed in the tibia 11 that are parallel spaced apart by 25 mm and lying in the medio-lateral plane of the tibia 11. A second blunt pin 34 is then positioned in the second hole 33.

Figure 11:
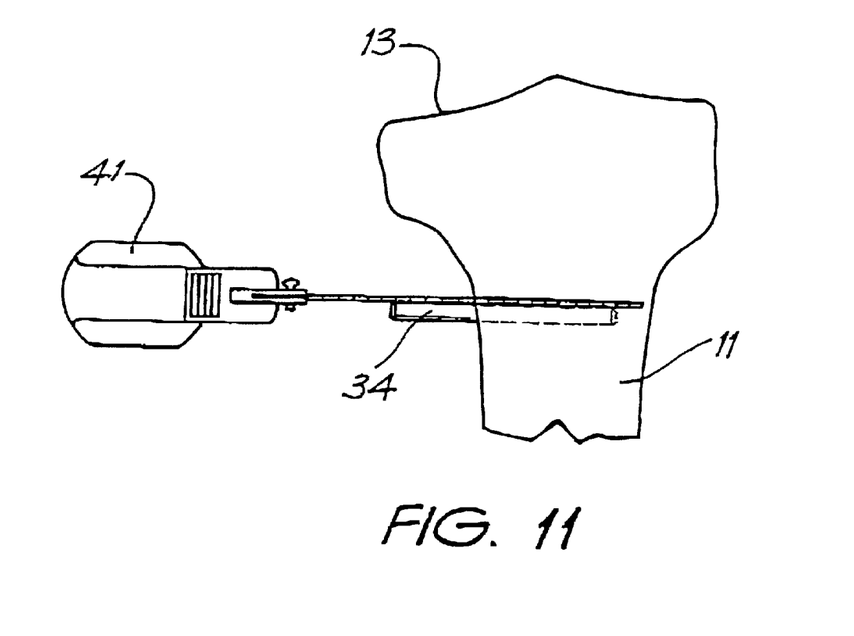
FIG. 11 is an anterior view of the tibia of FIG. 8 showing a reciprocating saw guided by the guide pins in the tibia resecting the tibia.
Figure 12:
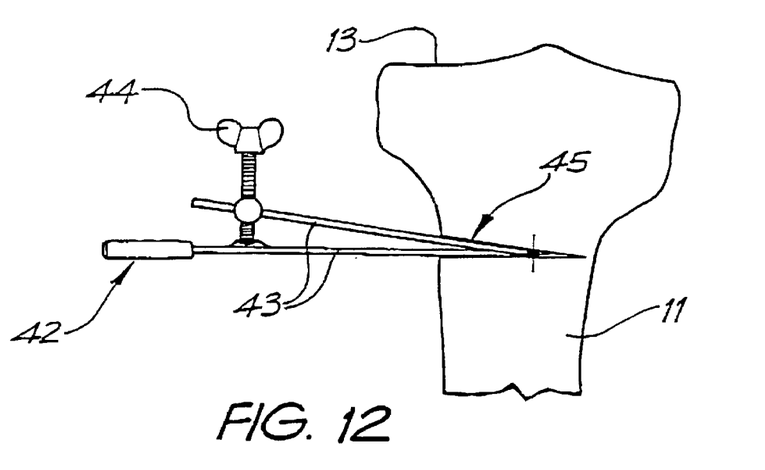
FIG. 12 is an anterior view of the tibia of FIG. 8 showing the cut formed by the reciprocating saw being widened with a wedging tool.

An oscillating saw 41 is then used to cut through the tibia 11 in a plane defined by the top edge of the pins 34. Using the measurement determined through the first of the holes 33 the saw cut is extended through the tibia 11 by an amount that is 5 mm less than the thickness of the tibia 11. A spreading tool 42 is then placed in the saw cut. The spreading tool comprises a pair of plates 43 hingedly connected together at one end, and a separating screw 44 threadedly engaged in one of the plates 43 and bearing on the other plate 43 with its free end. Rotation of the screw 44 in a clockwise fashion causes the plates 43 to separate at the end adjacent the screw 44. This separation in turn causes the gap 45 defined between the bone of the tibia 11 on either side of the cut to separate from the medial side of the tibia 11. The screw 44 is adjusted until the alignment of the tibia shows the desired correction, or over correction.

Figure 13:
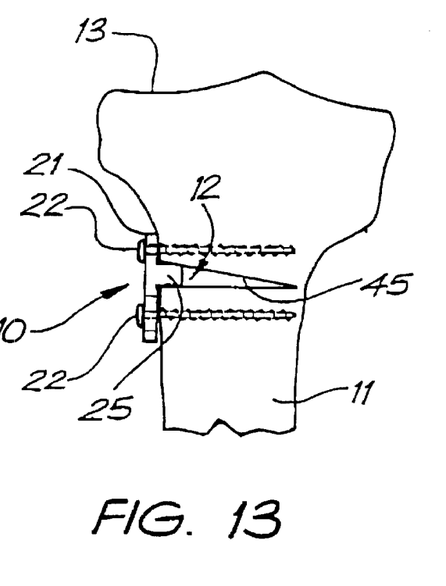
FIG. 13 is a vertical sectional view through the tibia of FIG. 8 in a frontal plane with a device as shown in FIGS. 5 to 7 positioned in the cut.
Figure 19:
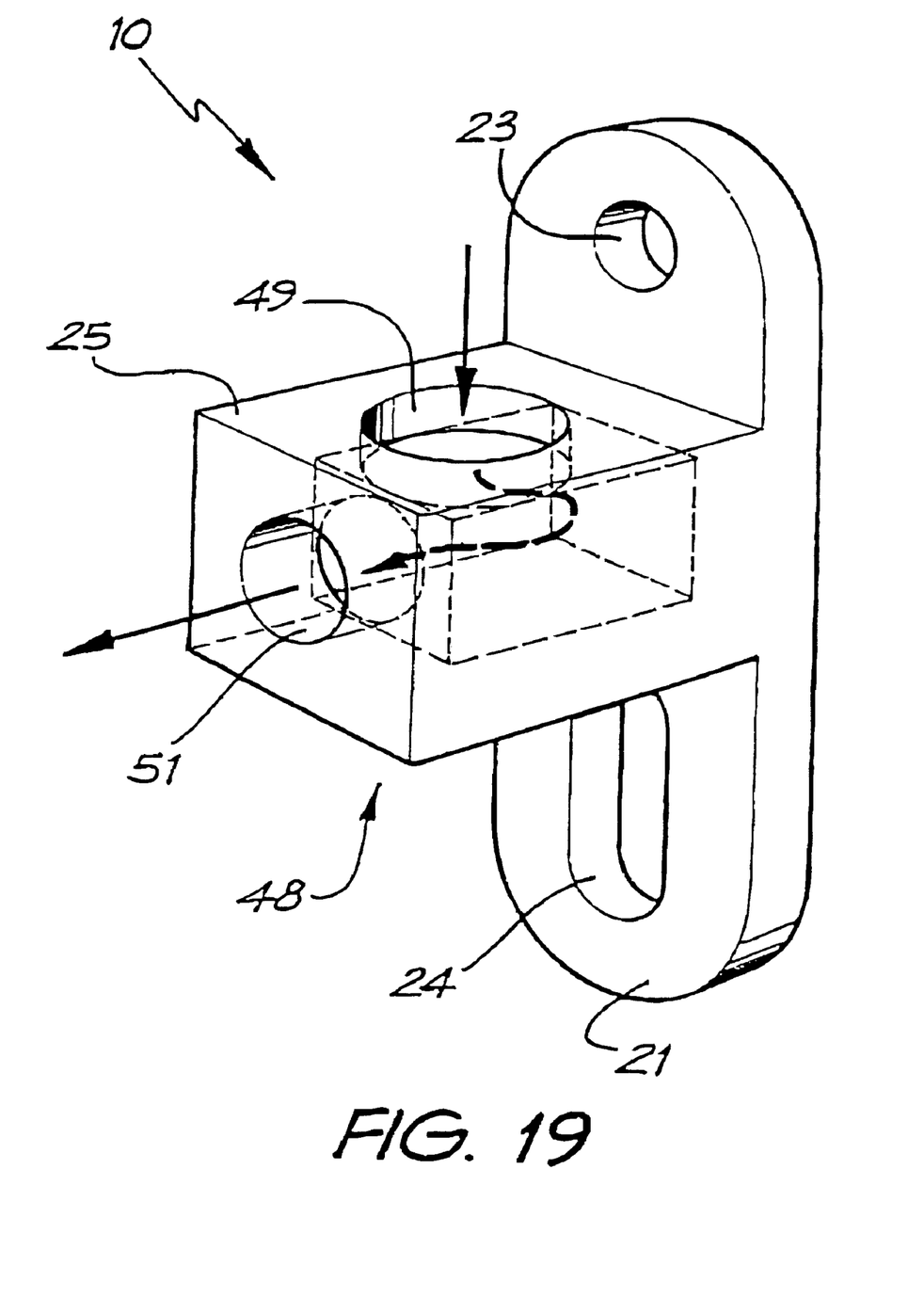
FIG. 19 is a perspective view of a device as shown in FIGS. 5 to 7 with a graphical illustration of a substance delivery system according to the present invention.

The surgeon then chooses one of the devices 10 that has a spacer member 25 with a width 'x' equal to the maximum width 12 of the gap 45. This device 10 is positioned with the spacer member 25 protruding into the gap 45 and touching the bone on either side of that gap. In this way, it is possible to ensure that a substance delivery system 48 with a first orifice 49 in a wall of the spacer member 25, adjacent to and in contact with the cortical bone on one side of the gap, is aimed such that a second orifice 51 of the substance delivery system 48 is pointed into the wedge osteotomy site. As blood exudes from the cut surface of bone, it leaks into the first orifice 49 in a wall of the spacer member 25 and causes any bio-active substance in the substance delivery system 48 to be forced out the second orifice 51 and into the wedge osteotomy site, being the desired site of action.

Figure 14:
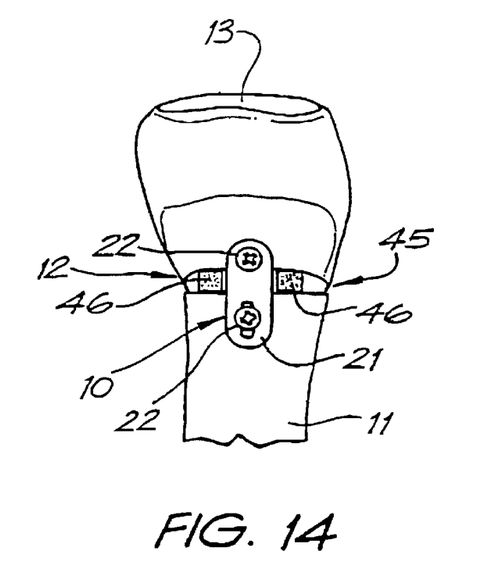
FIG. 14 is a medial view of the tibia of FIG. 13.
Figure 15:
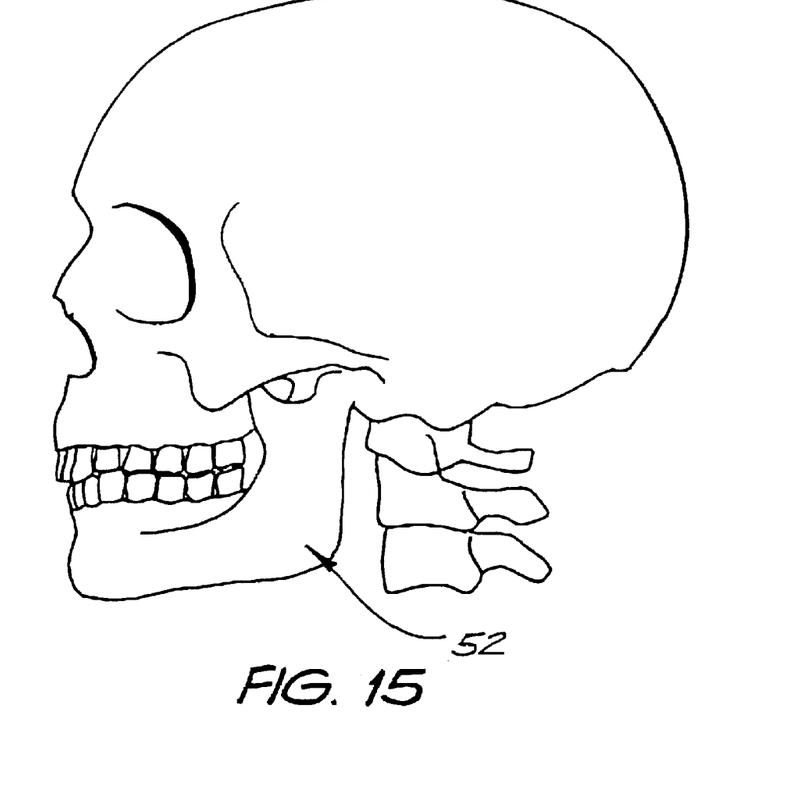
FIG. 15 is a lateral view of a skull of a patient showing the position of a mandible bone.

Holes are then drilled into the bone through the apertures 23 and 24 respectively and the plate member 21 is secured in place using securing means 22. Bi-cortical bone 46 harvested from the patients iliac crest 47 is the packed into the gap 45 on either side of the spacer member 25. The incision is then closed in the normal manner.

Figure 16:
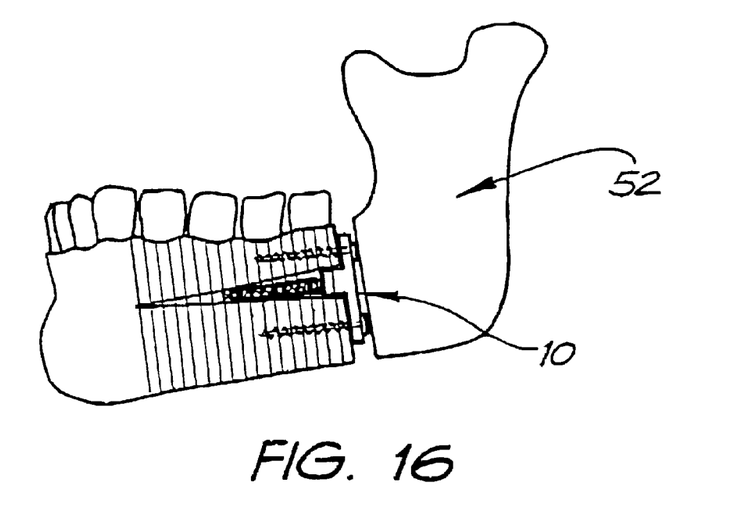
FIG. 16 is a lateral view of the mandible bone of FIG. 15 showing the result of a mandibular reconstruction; the mandible having within it, a wire gutter and a device as shown in FIGS. 5 to 7.
Figure 18:
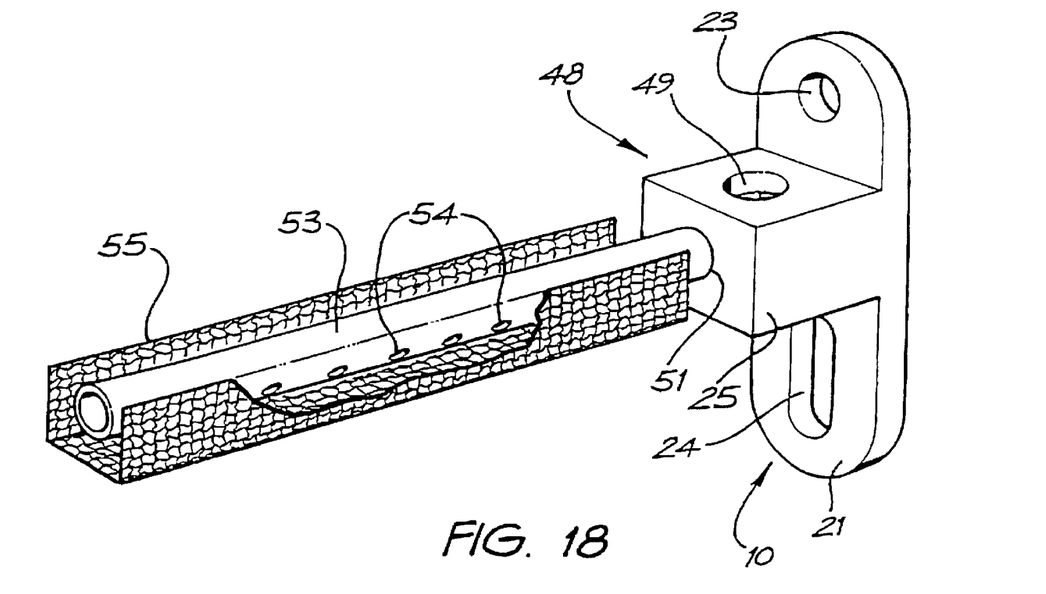
FIG. 18 is a perspective view of a preferred adaptation of a device as shown in FIGS. 5 to 7 with a tubular structure, having a plurality of orifices in its wall, connected to, or integral with, a second orifice in a wall of a spacer member of the device. In addition, this adaptation of the device is shown in its preferable position with respect to the wire gutter as illustrated in FIG. 17, both the device and the guidewire having been put in place during a mandibular reconstruction operation.

When the device 10 is to be used in the process of performing a mandibular reconstruction procedure (see FIG. 16), the device 10 is adapted for implantation into the body of a patient in order to be secured to a segment of the mandible bone 52. In this embodiment of the device 10, a tubular structure 53 is connected to, or integral with, a second orifice 51 in a wall of the spacer member 25, such tubular structure 53 having a plurality of orifices 54 in its wall.

Figure 17:
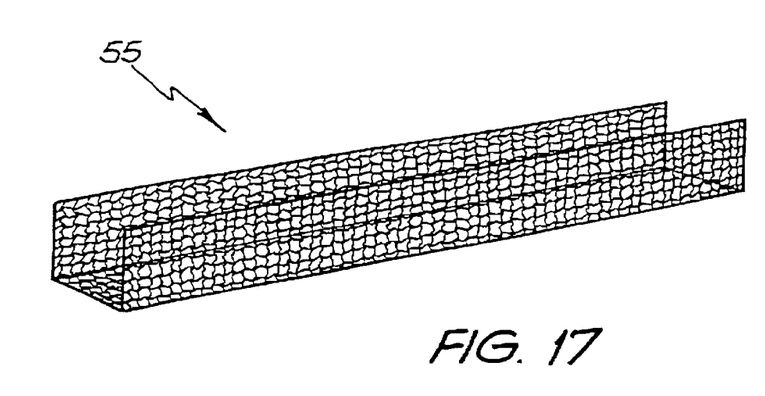
FIG. 17 is a perspective view of a wire gutter used in a mandibular reconstruction operation.

A mandibular reconstruction procedure often involves the use of a wire gutter 55 (as shown in FIG. 17) as a scaffolding upon which bone is expected to grow. The device 10 should be positioned such that the tubular structure 53 lines a trough of the wire gutter 55, having its plurality of orifices 54 pointing in the direction to which it is desirable to deliver at least one bio-active substance. This embodiment of the present invention provides a means by which bio-active substances, such as bone morphogenic protein, can be delivered to a surface of bone in order to encourage its growth. The location of the tubular structure 53 is extremely advantageous as its position helps to ensure that bone morphogenic protein, for example, is delivered to areas of bone in the vicinity of the wire gutter 55; such bone invariably growing along the gutter 55: a preferred outcome for the reconstruction procedure.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A device for use in surgery, the device comprising:
a plate member having a longitudinal axis, a first end, a first orifice adjacent the first end, a second end, and a second orifice adjacent the second end, wherein the first orifice is circular in shape and the second orifice is ovoid or elongate in shape, the second orifice having a long a diameter and a short diameter and being oriented such that the long diameter is longitudinally aligned with the longitudinal axis of the plate member, and
at least one spacer member which is engageable or integral with the plate member intermediate the first and second ends of the plate member, the spacer member having a built-in substance delivery system, comprising at least one chamber within the spacer member, and having at least two restricted orifices each cut into an individual surface of the spacer member, thereby providing a continuous passage through the first orifice, through the chamber of the substance delivery system, and through the second orifice, the substance delivery system being such that when the device has been placed in a desired location in the body of a patient a continuous force provided by the at least one substance or by a bodily fluid passing through the first orifice causes at least one selected substance to leak out through the second orifice and be delivered from the at least one space member into at least one designated site of action.

2. A device for delivering substances to a designated site of action in the body of a patient, the device comprising:
a plate member that is securable to a bone, the plate member having at least one spacer member that is engageable or integral with a face of the plate member, and
a substance delivery system housed by the at least one spacer member and comprising at least one chamber within the spacer member, and having at least two restricted orifices each cut into an individual surface of the spacer member, thereby providing a continuous passage through the first orifice, through the chamber of the substance delivery system, and through the second orifice, the substance delivery system being such that when the device has been placed in a desired location in the body of a patient a continuous force provided by the at least one substance or by a bodily fluid passing through the first orifice causes at least one selected substance to leak out through the second orifice and be delivered to a designated site of action in the body of a patient.

3. The device of claim 1 or 2, wherein securing means are used to secure the plate member to bone in the body of a patient.

4. The device of claim 1, wherein different shapes and sizes of both the plate member and the spacer member can be engaged as required to suit the circumstances of each case.

5. The device of claim 1, wherein the bodily fluid is blood leaking from a cut surface of bodily tissue.

6. The device of claim 1, further comprising a tubular structure extending from the second orifice, the tubular structure having at least one orifice.

7. The device of claim 2, wherein the bodily fluid is blood leaking from a cut surface of bodily tissue.

8. The device of claim 7, wherein the bodily tissue is bone.

9. The device of claim 2, further comprising a tubular structure extending from the second orifice, the tubular structure having at least one orifice.

10. The device of claim 9, wherein the tubular structure has a plurality of orifices, and provides a means for delivering a substance to a large surface of bone.

11. The device of claim 9, when used in the reconstruction of a mandible bone, wherein the tubular structure is placed within a trough of a wire mesh, the wire mesh being used as a scaffolding and support along which bone can grow.

12. The device of claim 1, wherein the size and shape of the spacer member and the plate member is adjustable.

13. A method for implanting a device according to claim 1, the method comprising:
   a) preparing any bio-active substance or combination of such substances to be delivered to a desired site of action, and loading such preparation into the substance delivery system in the spacer member;
   b) determining an appropriate location for the device so that the spacer member containing the bio-active substance delivery system is aimed in the direction of the desired site of action for the bio-active substance; and
   c) securing the device to a bone in the body of a patient.

14. The method of claim 13, wherein the longitudinal axis of the plate member is aligned with a longitudinal axis of a bone onto which the device is secured.

15. The method of claim 13, wherein a longitudinal axis of the plate member is aligned with a weightbearing axis of a bone onto which the device is secured, such that the second end of the plate member is anatomically distal the first end of the plate member.

16. A process for carrying out a high tibial osteotomy using a device according to claim 1, the process including the steps of:
   a) forming a saw cut in a tibia of a patient substantially in the medio-lateral plane adjacent to the head of the fibula;
   b) causing the cut to be widened on one side so as to bring the axis of the tibia into a desired alignment;
   c) placing the device such that the plate member spans the gap defined by the widened cut, the second end of the plate member is positioned on the distal side of the wedge osteotomy, and at least one spacer member protrudes into the gap defined by the widened cut such that cortical bone on either side of the gap is in contact with the spacer member; and
   d) securing the device to the tibia.

17. The process of claim 16, wherein after the tibia has been transected and the cut widened, a width of the gap between cut edges of bone is determined in order to select a device with an appropriately sized spacer member and plate member.

18. The process of claim 16 further comprising implanting various resorbable bases, such as resorbable bone fillers, along with the plate to provide additional structural benefit.

19. The process of claim 16, wherein the operation is performed on the side of the tibia that is most worn.

20. The process of claim 16, wherein the cut into the tibia stops short of cutting through the entire bone, such that an uncut section of cortical bone on the side opposite to the incision provides a stabilising means for the whole procedure.

21. The process of claim 16, wherein the cut is guided in the medio-lateral plane by a pair of rods placed into holes drilled in the tibia which are aligned with one another in that plane.

22. The process of claim 16, wherein a spreading tool is inserted into the cut in order to spread it to the desired extent.

23. The process of claim 22, where the spreading tool holds the tibia in the correct alignment while the plate member is affixed to the tibia.

24. The process of claim 16, further comprising packing the gap between the two faces of cut bone with bi-cortical bone harvested from the patient's iliac crest.

25. The process of claim 16, further comprising delivering to the gap between the two faces of cut bone a bone growth stimulating filler material, such as bone morphogenic protein.

26. The process of claim 25, wherein the bone growth stimulating filler material is delivered to the gap via the substance delivery system.

* * * * *